United States Patent [19]
Boss

[11] Patent Number: 5,779,477
[45] Date of Patent: Jul. 14, 1998

[54] METHOD AND APPLIANCE USING ONE OR MORE WIRE-FEEDING TRACKS FOR PRODUCTION OF ARTIFICIAL SUPPORTING MEMBERS FOR THE HUMAN BODY

[75] Inventor: Anders Boss, Molndal, Sweden

[73] Assignee: Nobel Biocare AB, Gothenburg, Sweden

[21] Appl. No.: 602,775

[22] PCT Filed: Jun. 30, 1995

[86] PCT No.: PCT/SE95/00809

§ 371 Date: Apr. 23, 1996

§ 102(e) Date: Apr. 23, 1996

[87] PCT Pub. No.: WO96/01082

PCT Pub. Date: Jan. 18, 1996

[30] Foreign Application Priority Data

Jul. 4, 1994 [SE] Sweden ................... 9402352

[51] Int. Cl.$^6$ ................................................. A61C 13/225
[52] U.S. Cl. ................................................. 433/172; 433/223
[58] Field of Search ................................. 433/223, 215, 433/180, 181, 182, 183, 172, 213, 25, 49

[56] References Cited

U.S. PATENT DOCUMENTS

| | | | |
|---|---|---|---|
| 5,052,928 | 10/1991 | Andersson | 433/172 |
| 5,195,890 | 3/1993 | Johansson et al. | 433/215 |
| 5,286,196 | 2/1994 | Brajnovic et al. | 433/173 |
| 5,419,700 | 5/1995 | Sillard | 433/172 |
| 5,630,717 | 5/1997 | Zuest et al. | 433/172 |

FOREIGN PATENT DOCUMENTS 2706281  12/1994  France  .................... 433/49

*Primary Examiner*—Cary E. O'Connor
*Attorney, Agent, or Firm*—Pollock, Vande Sande & Priddy

[57] ABSTRACT

A method for producing artificial supporting members in the human body is provided. In a first manufacturing stage, at least two support part members are matched together by machining contact surfaces on the supporting part members via which the supporting members are joined. Also during this stage, positional information regarding the relative positions of the contact surfaces and the supporting part members is identified. In a second manufacturing stage, the supporting part members are joined together using the positional information and are applied on a bearing member in relation to a plane. The plane extends at right angles with respect to a selected direction of the supporting member parts when they are in their matched positions. At least one of a wire feeding track and the bearing member are moved whereby the position of the wire feeding track is altered with respect to the plane. The wire feeding track is moved to cross connection portions of the supporting part members. As the wire feeding track crosses the connection portions, the supporting part member is machined to create a contact surface which can cooperate with another contact surface on another supporting part member. The positional information obtained during the first manufacturing stage is based on the positional relationship of the wire feeding track and the bearing member in the plane.

10 Claims, 3 Drawing Sheets

METHOD AND APPLIANCE USING ONE OR MORE WIRE-FEEDING TRACKS FOR PRODUCTION OF ARTIFICIAL SUPPORTING MEMBERS FOR THE HUMAN BODY

TECHNICAL FIELD

The present invention relates to a method for producing, by means of one or more wire-feeding tracks, artificial supporting members which can be in the form of dental bridges for use in the human body. The novel method includes two or more manufacturing stages in which, in a first manufacturing stage, at least two supporting member parts are matched together by machining of contact surfaces, via which the supporting member parts are joined together. In conjunction with the matching, positional information is obtained on the relative positions of the supporting member parts or of the contact surfaces. Positional information on the relative positions of the supporting member parts or of the contact surfaces is identified in the first manufacturing stage. In the second manufacturing stage, supporting member parts which have been matched are joined together using the identified information on the positions. The method utilizes a bearing member on which the supporting member parts are applied during the first manufacturing stage. The supporting member parts are moved or are placed in relation to a plane, for example a horizontal plane, which extends at right angles with respect to a selected direction, preferably the longitudinal direction, of the supporting member parts when these assume their mutually matched positions. The invention also relates to an appliance for accomplishing the method.

BACKGROUND OF THE INVENTION

It is already known from Swedish Patent 8605272-7 (455 156) to produce a dental bridge using two manufacturing stages. Positional information obtained from or in the first stage is used in the second manufacturing stage in order to simplify the adjustment work. The supporting member parts are matched to each other and machining members for producing contact surfaces between the supporting member parts for action of the supporting member parts in predetermined positions, which are transferred to the second subsidiary stage, which includes laser welding, adhesive bonding, etc., of the supporting member parts.

SUMMARY OF THE INVENTION

There is a need to be able to carry out the production of dental bridges in a manner which is simplified with respect to handling. The present invention solves this problem.

In accordance with the invention, one or more wire-conveying tracks are used in conjunction with production. It must be possible for the position of the wire-feeding tracks in relation to the bearing member, or rather in relation to a plane through the supporting parts arranged on the bearing member, to be adjusted. The invention also solves this problem.

The arrangement and the method concerning production of the supporting member will be able to permit a spark machining function in association with the bearing member and the supporting member parts which are arranged on the latter. The invention solves this problem.

There is a requirement to be able to automate the production process to a greater extent. The invention also solves this problem.

In order to achieve an efficient production method, it may be necessary, in the first subsidiary stage, to carry out machining of two contact surfaces simultaneously on one and the same supporting member part, i.e. on both sides of the supporting member part. The invention aims to solve this problem.

There is a need to be able to use one joining member (laser welding member) for serving several pairs of contact surfaces. The invention solves this problem and proposes movement in a given plane in an efficient and clearly defined manner.

It must be possible for a plurality of joining members to be used to serve two or more pairs of contact surfaces along the curved length of the dental bridge. The invention solves this problem.

A user-friendly arrangement with a spark machining unit and bearing members for supporting member parts is necessary for an efficient production procedure. The invention also solves this problem.

In some cases it is necessary, in connection with the production of a dental bridge, to design the bridge with an at least essentially plane top surface. The invention solves this problem by proposing that each wire-feeding track is able to attack the supporting member parts in more than one main direction, preferably two main directions which are at right angles to each other. According to the method of the invention, that the respective wire-feeding track and the bearing member are mutually displaced such that the position of the wire track in relation to the above mentioned plane is altered. At predetermined positions, the wire-feeding track crosses the connection portion(s) of the supporting member parts or an overlying portion (in the case where it is desired that the result of machining should have a straight top edge). The wire-feeding track is thus brought into contact with the respective supporting member part for establishing a contact surface or a compensating surface by means of a contact surface effected in a corresponding manner with the said wire-feeding track or a second wire-feeding track. The positional information identified in the second subsidiary stage is obtained by the indication of the positional relationship in the plane, during the said first subsidiary stage, between the respective wire-feeding track and the bearing member.

The respective wire-feeding track and the bearing member will be mutually displaceable in order to bring about changes in the relative position of the wire track in relation to the plane. At predetermined positions, the wire-feeding track crosses the connection portion of the supporting member parts, or crosses those parts of the supporting member parts which are being machined. The identifiable positional information which is used in the second subsidiary stage can be related to the mutual positional relationship of the wire-feeding track and of the bearing member in the plane during the first subsidiary stage.

In one embodiment, the wire-feeding track constitutes a first subsidiary track in a common wire-feeding track. In the latter, the first subsidiary track merges into second and third subsidiary tracks via switching members. In another embodiment, the bearing member or supporting member part bears on a portion directed towards a user or operator. The wire-feeding track and the bearing member are arranged to permit monitoring of the mutual movements at the portion. Moreover, the wire-feeding track or wire-feeding tracks can form part of one or more wire sparking units or spark machining units which can be of a known type.

In a further embodiment, the bearing member is arranged to assume a fixed position in terms of angle of an rotation. Supporting member parts included in a dental bridge can thus be arranged with positions which concur with a curved length, which corresponds essentially to all or part of the shape of a jaw. Two wire-feeding tracks are arranged on both sides of a dividing line or radius through the curved length. In an alternative embodiment, one wire-feeding track can be moved between different working positions in conjunction with the bearing member. The plane can be essentially parallel with respect to the top surface of the bearing member. The relative movement between the bearing member and the respective wire-feeding track consists essentially of a parallel displacement of either the track or the bearing member. Alternatively, both the track and the bearing member can be movable.

In a further embodiment, in the case where there are essentially uniformly shaped cross-sectional areas of the connection portions between different pairs of supporting member parts, use is made of a movement function for contact surfaces of the first connection portions to a member serving all the connection portions and contact surfaces. The movement can take place in the plane to a common joining position for joining members, for example, laser welding electrodes, or adhesive bonding members, etc. The joining position can be arranged at second, third, etc., connection portions/contact surfaces or between two pairs of connection portions/contact surfaces. The movement of the connection portions or of the contact surfaces to the joining position is arranged preferably to take place with uniform, predetermined distribution of the movement or movements in question. In an alternative embodiment, a plurality of joining members, or joining positions by means of the joining members, are arranged along the curved length. Each wire-feeding track is arranged such that it attacks or crosses the supporting member parts in two main directions, arranged at right angles to each other, for establishing the machining function. Thus, in the first direction, the wire-feeding track cuts connection portions on the supporting member parts. In the second direction, the wire-feeding track can cut or machine the supporting member parts to form a straight top edge on the dental bridge, or to form an adaptation surface in the mouth, etc.

An advantage of the present invention is that bridge constructions can be used which are known and have been tried and tested. Supporting member parts which can be arranged on implants in the jaw bone can be matched in the bridge construction work and can be joined together with the prescribed accuracy, which is normally 0.01–0.02 mm. Position-identifying members and arrangements of a known type can be used, i.e. stored between the manufacturing stages and transferred to the second subsidiary stage when the latter is to be carried out. The second subsidiary stage can be followed by a third subsidiary stage for obtaining a straight top surface on the dental bridge, or for achieving the adaptation, etc.

DESCRIPTION OF THE FIGURES

A presently proposed embodiment of a method and according to the invention invention will be described hereinbelow with reference to the attached drawings, in which.

DETAILED DESCRIPTION OF THE INVENTION

Figure 1:
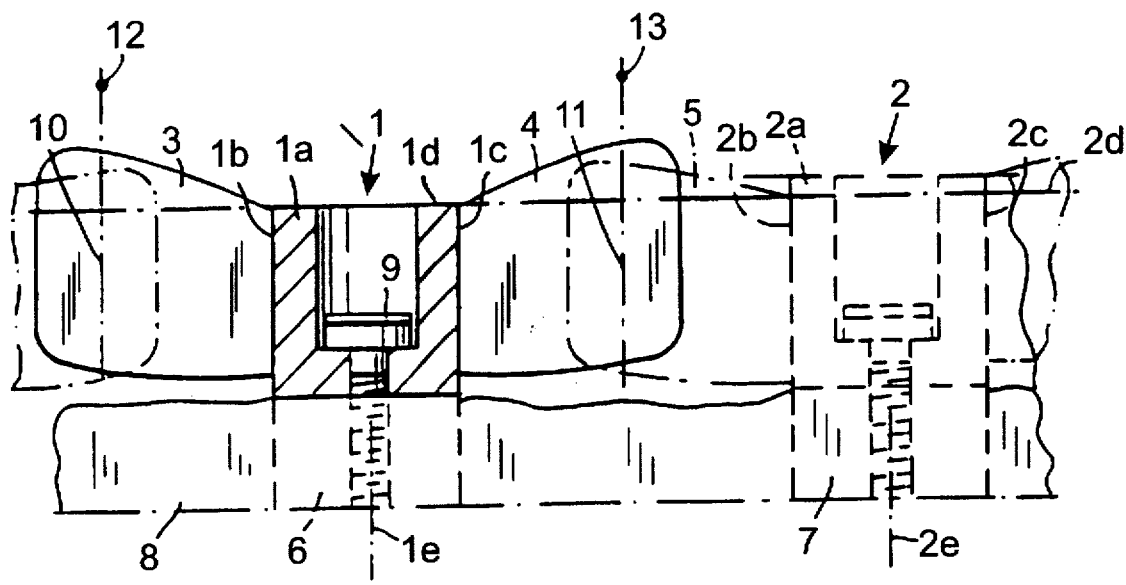
FIG. 1 shows from the side, and in partial section, supporting member parts arranged in a bearing.

The supporting member parts in a dental bridge can comprise a first supporting member part 1 which is shown by full lines, and a second supporting member part 2 which is shown by broken lines in FIG. 1. Each supporting member part, has a fastening part 1a and 2a, respectively. Wing-shaped members 3, 4 and 5, respectively, extend from the fastening part, for example from the diametrally opposite sides 1b, 1c and 2b, 2c, respectively, of the fastening part. The supporting member parts are intended to be fastened in an implant 6 or 7, respectively, in a jaw bone 8. The supporting member parts are in this case secured by means of screws 9 in a manner known manner.

In accordance with the invention, the supporting member parts will be matched via their wings 3, 4 and 5, respectively, in order to form a composite dental bridge which can be joined together. The wing-shaped elements 3, 4 and 5, respectively, will in this case be machined or cut such that contact surfaces are established between the wings on the various supporting member parts. Such cut surfaces or contact surfaces are symbolized in FIG. 1 by 10 and 11, respectively.

A model of the jaw bone 8 is used during the matching and the joining process. The implants 6 and 7 are arranged in the model in a known manner. Each supporting member part is applied on its associated implant, supporting member part 1 is applied on the implant 6, or rather its representation in the model. With each supporting member arranged in the model, the wings of the supporting member part are cut or sliced, i.e. the wings 3 and 4 in the case of the supporting member part 1. The supporting member in question is thereafter removed from the model, and the second supporting member part 2 is then fastened in place in the model. The sectioning or cutting of the wings of this supporting member part, wing 5 in FIG. 1, is then carried out in a corresponding manner in order to form the contact surface with respect to the wing of the supporting member part 1, i.e. the wing 4 in this case. In this way, contact surfaces are created on the various supporting member parts of the dental bridge.

In accordance with the invention, at least one wire-feeding track is used for the production or cutting of the contact surfaces 10, 11. FIG. 1 shows a case in which two wire-feeding tracks 12 and 13 are used in parallel. It is possible to move the position of the wire-feeding track 12 to the position of the wire-feeding track 13 if only one wire-feeding track is used.

Figure 2:
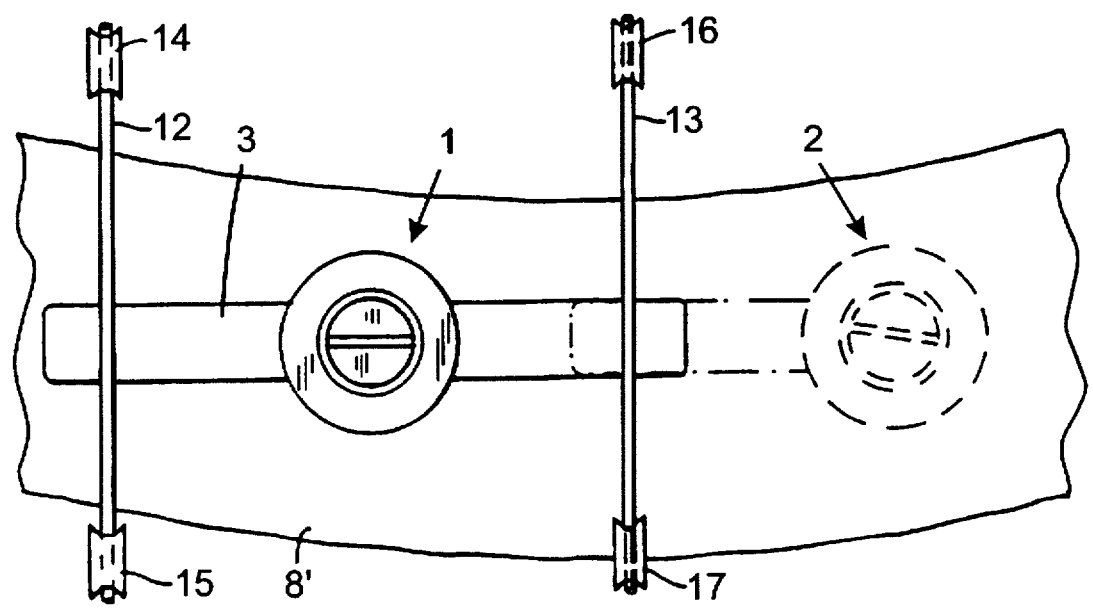
FIG. 2 shows a plan view of the supporting members according to FIG. 1, to which there run wire-feeding tracks arranged in conjunction with connection portions of the supporting member parts.

FIG. 2 shows the arrangement of FIG. 1 as seen from above. The thickness of the wires in the wire-feeding tracks 12 and 13 is shown in an exaggeratedly thick representation for the sake of clarity. The wire-feeding tracks 12 and 13 run via deflection members or rollers 14, 15 and 16, 17, 20 respectively. The shape of the jaw or of the model 8' is a curved shape. The matched and joined supporting member parts will extend essentially along this curve shape.

Figure 3:
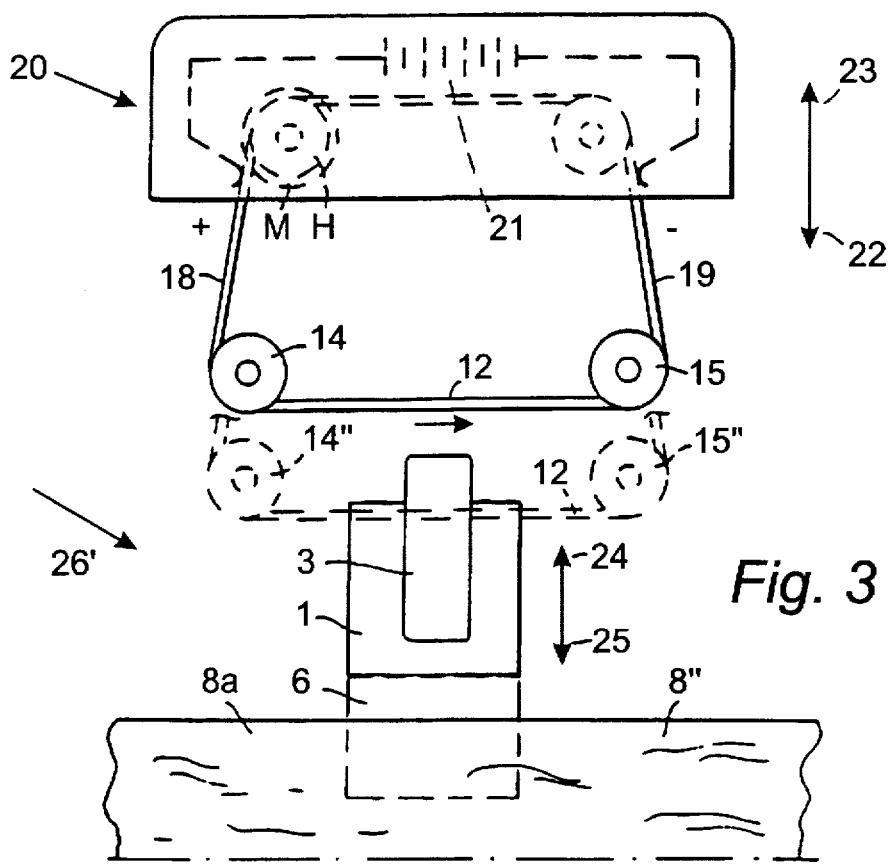
FIG. 3 shows a side view of a spark machining unit arranged on a bearing part, on which a supporting member part is arranged.

FIG. 3 shows the arrangement of FIGS. 1 and 2 viewed from the side, in which the deflection members or the rollers 14 and 15 are shown. The wire-feeding track 12 is included as a subsidiary track in a common track which also comprises the track sections 18 and 19. The common track forms part of a spark machining unit 20, which can be of a type known. In the spark machining unit, one track section 18 is made positive and the other track section 19 is made negative by connections to positive and negative voltages, for example a battery 21, in a known manner. The unit 20 is arranged to be vertically displaceable in the directions of the arrows 22 and 23. FIG. 3 shows the unit in a lowered position, indicated with broken lines for the deflection wheels 14 and the wire track 12. The model 8" or the bearing member associated with implant 6 can either be fixed or can be displaced vertically in the directions of the arrows 24 and 25. Alternatively, the unit can be essentially fixed, and the bearing member can be vertically displaceable. By means of the relative vertical displacements between the unit and the bearing member/the supporting member parts, the wire-feeding track 12 can be made to cross the lengths of the joining portions, i.e. the wings 3, 4 and 5. Upon the crossing function, the wire-feeding track 12 is brought into cooperation with the respective supporting member part, via its connection portion. Upon this cooperation, the portion in question is cut or machined in order to creat the contact surface (cf. 12 and 11, respectively, above). An operator has a good overview of the machining in the direction of the arrow 26. The bearing member or the model thus bears the supporting member part at a portion 8a of the model or a bearing portion where the good view can be established.

Figure 4:
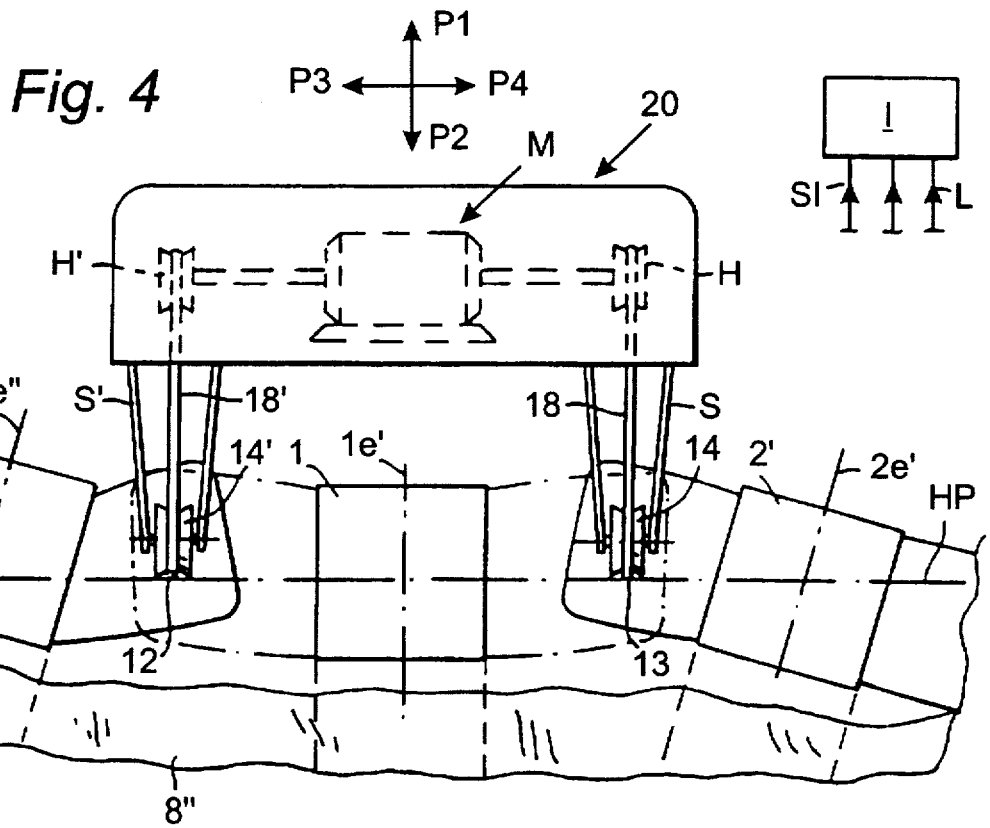
FIG. 4 shows from the front, i.e. from the direction of the operator, the spark machining unit, supporting member parts, jaw section according to FIGS. 2 and 3.

FIG. 4 shows the unit 20 from the front, as well as the model 8'. In this case the axes of the supporting member parts have been shown by 1e', 1e " and 2e'. The axes 1e" and 2e' are in this case shown inclined, as is the associated implant. Contact surfaces can also be arranged on such inclined supporting member parts with the present arrangement. The parallel wire-feeding tracks 12 and 13 have been shown together with the track section 18 (or 18') described in connection with FIG. 3. Each common track is driven in a known manner with motor arrangement M acting on drive wheels H and H', respectively. The deflection wheels 14 and 14' are braced on struts S and S', respectively. According to the above, the unit can be moved in the vertical direction in the directions of the arrows P1 and P2. In the present case the unit can also be moved in laterally in the direction of the arrows P3 and P4 for moving the wire tracks 12 and 13, respectively, in a horizontal plane HP through the supporting member parts 1 and 2', 2", respectively. A member for collecting information on the unit, i.e. the positions of the wire-feeding tracks 12, 13 in the plane HP, is contained in a unit I for use in the joining stage shown in FIG. 5 and described hereinafter. The information-collecting member is symbolized by IS. The information identification or the information collection is symbolized by connections L and signal information SI.

Figure 5:
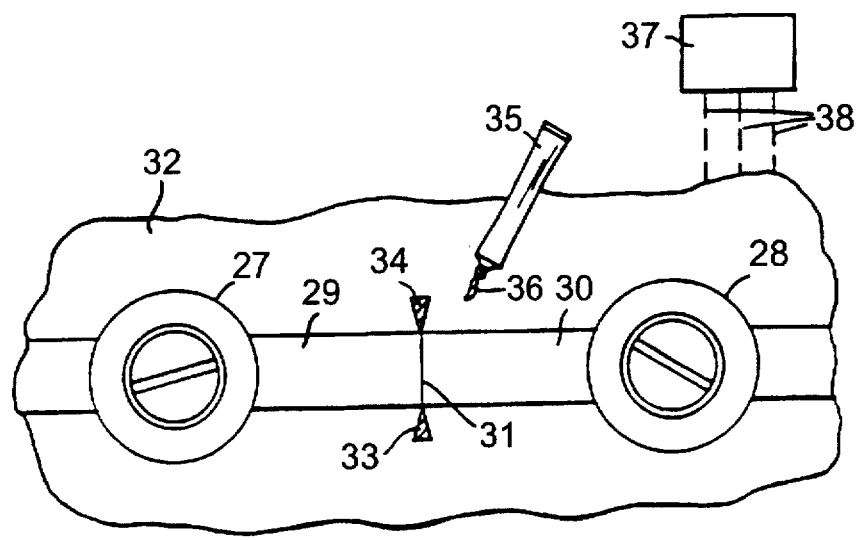
FIG. 5 shows a plan view of supporting member parts and of joining members (laser welding electrodes) arranged on these.

In FIG. 5, two supporting member parts are shown by 27 and 28. The connection portions of the supporting member parts are indicated by 29 and 30. In a first manufacturing stage in accordance with the above, matching of the supporting member parts has taken place, and the contact surfaces between their connection portions 29, 30 have already been established. The contact surfaces are symbolized by 31. The FIG. 5 is shows the second manufacturing stage in which the supporting member parts are actually joined to form a dental bridge. Each contact surface pair is set up in the model 32, and joining takes place, for example, by means of laser welding, with FIG. 5 showing two electrodes 33 and 34 which are associated with a laser welding unit. Alternatively, the joining of the contact surfaces can be effected by means of an adhesive bonding member 35, by means of which adhesive 36 is applied in the seams or joints in question. The joining preferably takes place at the same positions where the formation of the contact surfaces has been carried out. Positional information on the formed contact surfaces can be obtained in a known manner from the first manufacturing stage. The positional information can be included in the second manufacturing stage, and members containing the positional information are symbolized by 37 in FIG. 5. The action on, or adjustment of, the model or the bearing member 32 has been symbolized in FIG. 5 by connections 38.

Figure 6:
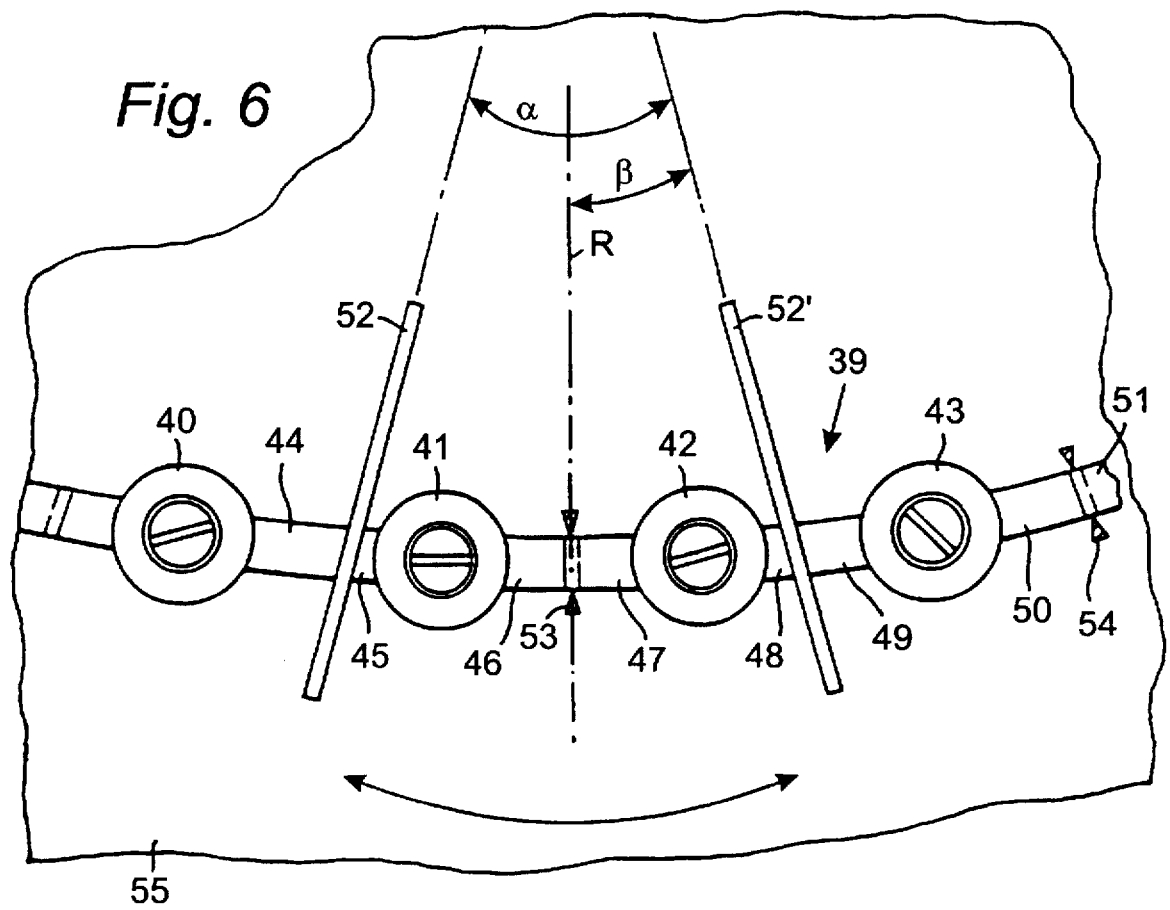
FIG. 6 shows a plan view of a dental bridge which is made up of supporting member parts and on which wire-feeding tracks and joining members are arranged.

In FIG. 6, a dental bridge which has been matched and produced is shown by 39. In the horizontal section shown, the dental bridge has a curved shape which essentially corresponds to all or part of the shape of a jaw. In FIG. 6, four supporting member parts 40, 41, 42 and 43 are indicated with matched connection portions 44, 45; 46, 47; 48; 49 and 50; 51, etc., respectively. In accordance with FIG. 1, a wire-feeding track 52 can be used and is moved between different machining positions. Thus, the wire-feeding track 52 can assume the position 52'. Alternatively, two wire-feeding tracks can be used for positions 52 and 52', respectively, etc. In FIG. 6, an angle alpha is use to show the distance between the different positions of the wire-feeding track 52. An angle beta shows the angular position or angular distance [lacuna] track position. The angular positions identified and are stored upon production of the contact surfaces and are used during the joining stage. The bearing member 55 can be fixed from the point of view of the angle of rotation or can be moved from the point of view of the angle of rotation. In accordance with the above, the wire-feeding tracks can also be fixed or can be moved in the horizontal plane shown by FIG. 6. This also applies to the various working positions of the electrodes 53 and 54. With the present invention it is possible to obtain an optimal manufacturing function for each individual case by using one or more wire-feeding tracks, one or more welding units, a fixed or movable position of rotation of the bearing member 55, etc. The information on angular or parallel displacement which is available in the first manufacturing stage is transferred, in accordance with the above, to the second manufacturing stage and can be used in the spark machining arrangement or in the welding arrangement.

In accordance with FIG. 1, the finished bridge or supporting member parts can be subjected to further treatments. Thus, for example, the supporting member parts can be machined with the wire-feeding track or wire-feeding tracks so that a straight top edge 1d, 2d (FIG. 1) is formed on the finished bridge despite the fact that the bearing axes 1e and 2e, respectively, of the supporting member parts and the implant are inclined. Spark machining is substantially quicker than cutting, for example, with roller, possibly 10 times quicker.

The invention is not limited to the embodiment which is described above as an example, but instead can be modified within the scope of the patent claims which follow and the inventive concept.

I claim:
1. A method for producing artificial supporting members in the human body, wherein, in a first manufacturing stage, at least two supporting part members are matched together by machining contact surfaces on said supporting member parts via which said supporting part members are joined and positional information regarding the relative positions of said contact surfaces and supporting part members is identified, and in a second manufacturing stage, said supporting part members are joined together using said positional information and said supporting part members are applied on a bearing member in relation to a plane, said plane extends at right angles with respect to a selected direction of said supporting part members when they are matched together, said method comprising the steps of:

moving at least one of a wire feeding track and said bearing member such that the position of said wire feeding track is altered with respect to said plane;

crossing connection portions of said supporting part members with said wire feeding track during said moving;

machining said supporting part member with said wire feeding track to create a contact surface at said connection portion, said contact surfaces being able to cooperate with another contact surface on another supporting part member; and obtaining said positional information based on the positional relationship of said wire feeding track and said bearing member in said plane during said first manufacturing stage.

2. A method according to claim 1 further comprising the steps of:

arranging said bearing member to have a fixed angle of rotational position;

arranging said supporting member parts in a dental bridge to form a curved length; and moving one wire feeding track between working positions.

3. A method according to claim 2 further comprising the step of arranging two wire feeding tracks on both sides of a radius through said curved length.

4. A method according to claim 1 wherein said plane is essentially parallel with a top of said bearing member, further comprising the step of:

moving at least one of said bearing member and said wire feeding track in a parallel displacement.

5. A method according to claim 1 further comprising the steps of: moving said contact surfaces to a joining position with a predetermined uniform movement.

6. A method according to claim 1 further comprising the steps of: arranging said wire feeding track in two positions, a first position and a second position which are at right angles to each other, in said first position said wire feeding track cuts contact surfaces on said supporting member parts and in said second position it cuts supporting member parts to from a straight top edge.

7. A method according to claim 1 wherein a uniform cross section area of contact surfaces exist between different pairs of supporting member parts, said method further comprising the step of moving said contact surfaces to joining positions where a means for joining joins said contact surfaces together.

8. An apparatus for making artificial supporting members in a human body, each supporting member being made of at least two supporting member parts, wherein, in a first manufacturing, at least two supporting member parts are matched together by machining contact surfaces via which said supporting member parts are joined and positional information on the relative positions of said contact surfaces and supporting part members is identified, and in a second manufacturing stage, said supporting member parts are joined together using said positional information and said supporting member parts are applied on a bearing member in relation to a plane, said apparatus comprising:

a spark machining unit;

at least one wire feeding track attached to said spark machining unit;

first means for moving at least one of said wire feeding track and said bearing member whereby said wire feeding member crosses connection portions of said supporting member parts at predetermined positions; and second means for identifying positional information of said wire feeding track and said bearing member, communicating with said first means.

9. The apparatus of claim 8 wherein said wire feeding track comprises a first subsidiary track arranged in a plane horizontal to said bearing member; deflection members located at ends of said first subsidiary track; and second and third subsidiary tracks extending from opposite ends of said first subsidiary track, partially around said deflection members and into said spark machine unit.

10. The apparatus of claim 8 wherein said bearing member bears said supporting member part on a portion directed towards an operator, said wire feeding track and said bearing member being arranged to move at said portion.

* * * * *